(12) United States Patent
Anson et al.

(10) Patent No.: US 7,736,377 B1
(45) Date of Patent: Jun. 15, 2010

(54) DEVICES AND METHODS FOR THE REPAIR OF ARTERIES

(75) Inventors: Anthony Walter Anson, Middlesex (GB); Brian Ridley Hopkinson, Nottingham (GB); Syed Waquar Yusuf, Nottingham (GB)

(73) Assignee: Anson Medical Limited (GB)

( * ) Notice: Subject to any disclaimer, the term of this patent is extended or adjusted under 35 U.S.C. 154(b) by 0 days.

(21) Appl. No.: 09/762,223

(22) PCT Filed: Aug. 3, 1999

(86) PCT No.: PCT/GB99/02544

§ 371 (c)(1),
(2), (4) Date: May 7, 2001

(87) PCT Pub. No.: WO00/07506

PCT Pub. Date: Feb. 17, 2000

(30) Foreign Application Priority Data

Aug. 3, 1998 (GB) .................................. 9816800.8
Aug. 3, 1998 (GB) .................................. 9816802.4

(51) Int. Cl.
*A61B 17/08* (2006.01)
(52) U.S. Cl. ...................... 606/219; 606/153
(58) Field of Classification Search .............. 606/219, 606/75, 154, 155, 156, 216, 151, 153, 213, 606/215, 188; 623/1.36; 24/67.9, 67 P, 350, 24/377, 380; 411/457–460, 468, 515, 530
See application file for complete search history.

(56) References Cited

U.S. PATENT DOCUMENTS

| | | | |
|---|---|---|---|
| 1,036,229 A | * | 8/1912 | Harrild ........................ 411/458 |
| 1,109,967 A | | 9/1914 | Condon |
| 1,150,358 A | * | 8/1915 | Gilmer ........................ 411/460 |
| 2,108,206 A | | 2/1938 | Meeker |
| 3,527,223 A | * | 9/1970 | Shein ........................ 606/188 |
| 3,716,058 A | | 2/1973 | Tanner |
| 3,814,104 A | | 6/1974 | Irnich et al. |
| 3,868,956 A | | 3/1975 | Alfidi et al. |
| 4,275,813 A | * | 6/1981 | Noiles ........................ 206/339 |
| 4,317,451 A | * | 3/1982 | Cerwin et al. ................. 227/19 |
| 4,485,816 A | * | 12/1984 | Krumme ....................... 606/219 |
| 4,590,938 A | | 5/1986 | Segura et al. |

(Continued)

FOREIGN PATENT DOCUMENTS

DE 197 11 288 A1 1/1998

(Continued)

*Primary Examiner*—Julian W Woo
(74) *Attorney, Agent, or Firm*—Craig A. Fieschko, Esq.; DeWitt Ross & Stevens S.C.

(57) ABSTRACT

A device for retaining a graft on an artery, comprising a first part for contacting the graft and a second part for contacting the artery when the device is pierced radially through the graft and the artery wall, the first and second parts being connected by a resilient member, wherein the resilient member biases the first and second parts towards each other into a retaining configuration such that in use the artery and the graft are retained together between the first and second parts of the device, and wherein the first and second parts are moveable into an open configuration in which they are further apart than in the retaining configuration to enable the device to be conveyed along an artery.

25 Claims, 12 Drawing Sheets

U.S. PATENT DOCUMENTS

| | | | |
|---|---|---|---|
| 4,921,484 A | | 5/1990 | Hillstead |
| 5,002,562 A | | 3/1991 | Oberlander |
| 5,030,224 A | | 7/1991 | Wright et al. |
| 5,042,707 A | | 8/1991 | Taheri |
| 5,192,291 A | | 3/1993 | Pannek |
| 5,192,303 A | | 3/1993 | Gatturna et al. |
| 5,219,358 A | * | 6/1993 | Bendel et al. ............... 606/222 |
| 5,222,971 A | | 6/1993 | Willard |
| 5,263,973 A | * | 11/1993 | Cook ........................ 606/215 |
| 5,282,845 A | | 2/1994 | Bush et al. |
| 5,330,490 A | | 7/1994 | Wilk |
| 5,411,522 A | | 5/1995 | Trott |
| 5,413,584 A | * | 5/1995 | Schulze ..................... 227/19 |
| 5,531,760 A | | 7/1996 | Alwafaie |
| 5,540,716 A | * | 7/1996 | Hlavacek .................. 227/902 |
| 5,573,543 A | | 11/1996 | Akopov et al. |
| 5,586,983 A | * | 12/1996 | Sanders et al. ............... 606/61 |
| 5,618,311 A | | 4/1997 | Gryskiewicz |
| 5,632,746 A | | 5/1997 | Pyka et al. |
| 5,720,755 A | | 2/1998 | Dakov |
| 5,820,628 A | | 10/1998 | Middleman et al. |
| 5,893,856 A | | 4/1999 | Jacob et al. |
| 5,984,949 A | * | 11/1999 | Levin ........................ 606/216 |
| 5,990,378 A | | 11/1999 | Ellis |
| 5,997,556 A | | 12/1999 | Tanner |
| 6,071,292 A | * | 6/2000 | Makower et al. ............ 606/139 |
| 6,093,205 A | | 7/2000 | McLeod et al. |
| 6,113,611 A | * | 9/2000 | Allen et al. ................. 606/151 |
| 6,132,438 A | * | 10/2000 | Fleischman et al. ......... 606/151 |
| 6,190,401 B1 | * | 2/2001 | Green et al. ................ 227/902 |
| 6,200,330 B1 | * | 3/2001 | Benderev et al. ............ 606/232 |
| 6,228,055 B1 | | 5/2001 | Foerster et al. |
| 6,273,903 B1 | * | 8/2001 | Wilk .......................... 606/142 |
| 6,287,315 B1 | * | 9/2001 | Wijeratne et al. ........... 606/108 |
| 6,334,867 B1 | | 1/2002 | Anson |
| 6,419,686 B1 | | 7/2002 | McLeod et al. |
| 6,447,524 B1 | * | 9/2002 | Knodel et al. ............... 606/151 |
| 6,451,034 B1 | * | 9/2002 | Gifford et al. ............... 606/153 |
| 6,485,496 B1 | * | 11/2002 | Suyker et al. ............... 606/153 |
| 6,749,622 B2 | | 6/2004 | McGuckin et al. |
| 6,994,713 B2 | * | 2/2006 | Berg et al. .................. 606/153 |
| 2005/0165305 A1 | | 7/2005 | Foerster et al. |

FOREIGN PATENT DOCUMENTS

| | | |
|---|---|---|
| EP | 0820729 | 1/1998 |
| FR | 2725126 | 4/1996 |
| FR | 2 725 126 A1 | 5/1996 |
| FR | 2746292 | 9/1997 |
| WO | WO 92/05828 | 4/1992 |
| WO | WO 96/08208 A2 | 3/1996 |
| WO | 98/02100 A1 | 1/1998 |
| WO | 99/00074 A1 | 1/1999 |
| WO | WO 99/00055 A2 | 1/1999 |
| WO | 99/07292 A1 | 2/1999 |
| WO | 99/37242 A1 | 7/1999 |
| WO | 00/07506 A2 | 2/2000 |
| WO | 01/30269 A1 | 5/2001 |

* cited by examiner

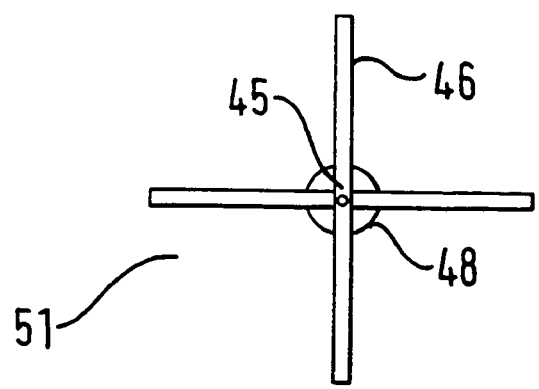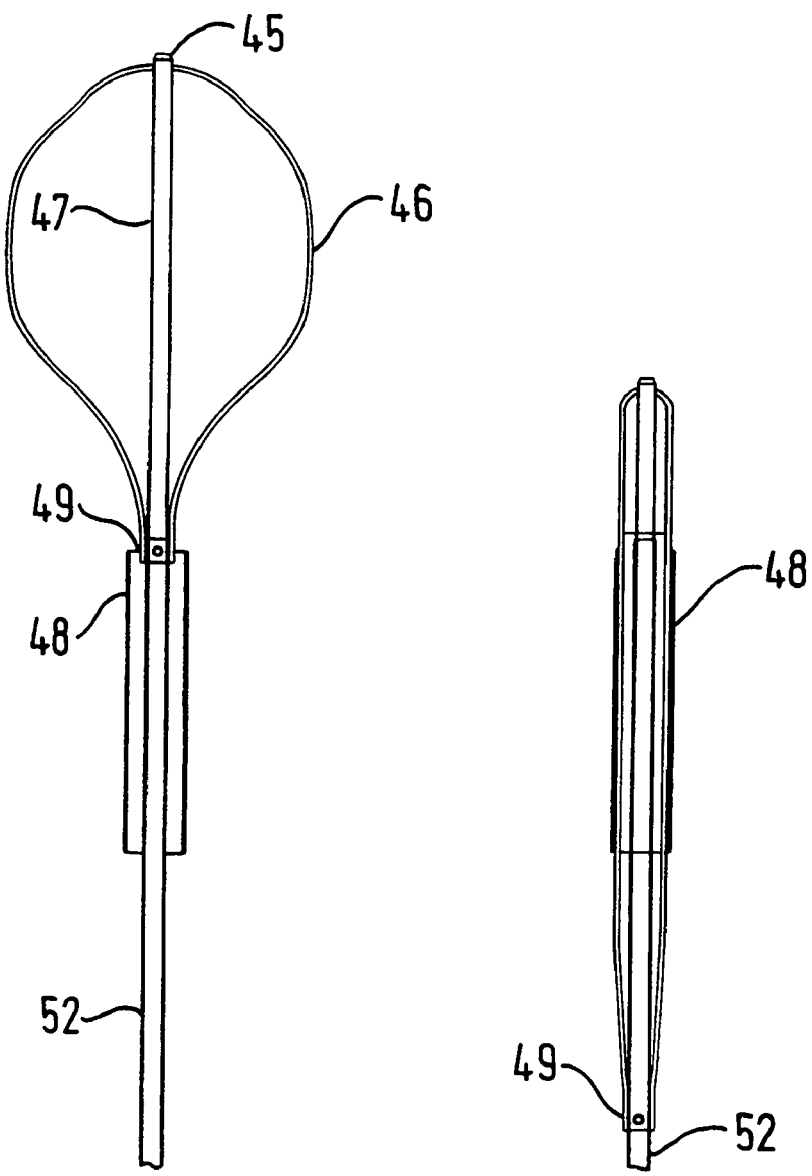
FIG. 10

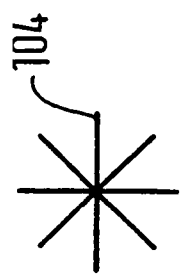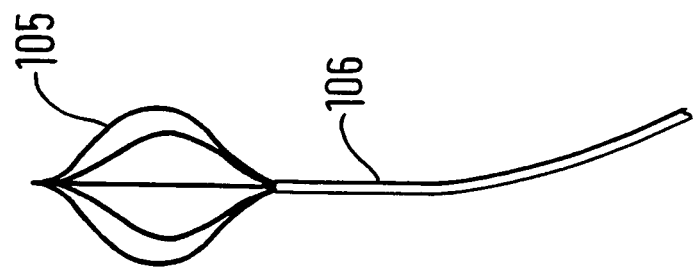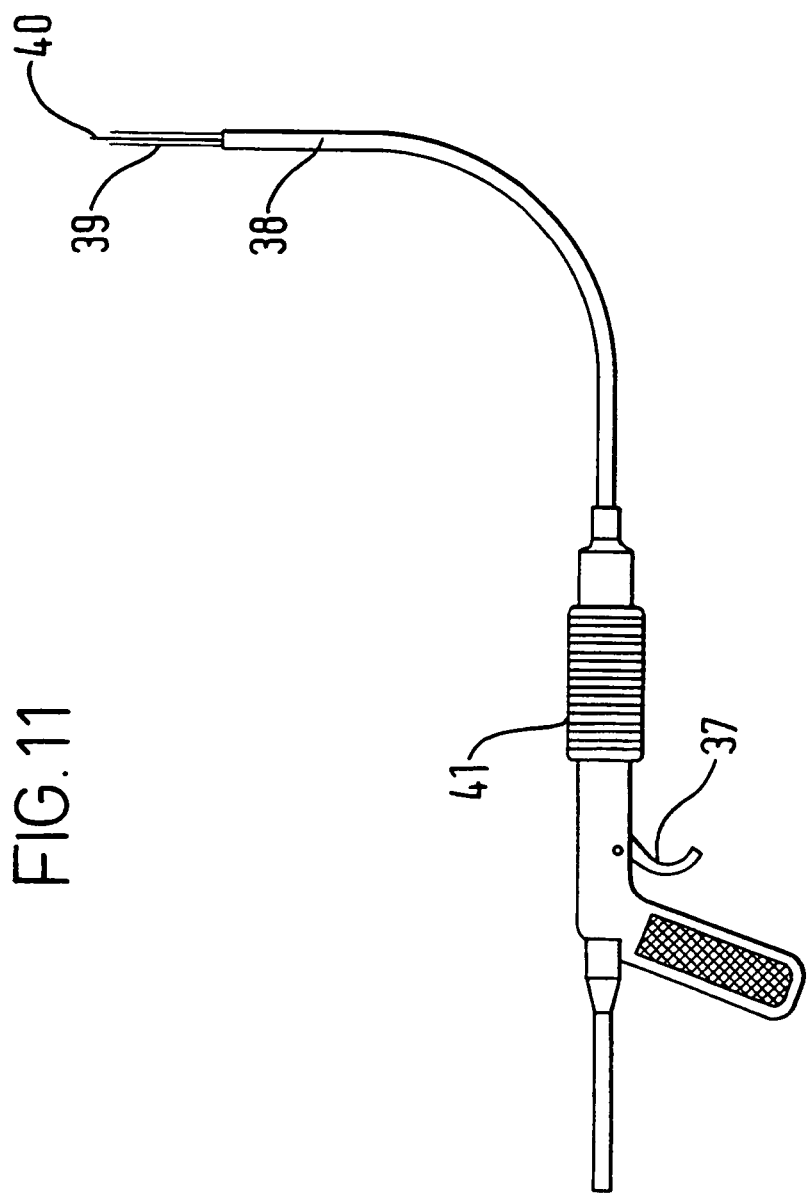
FIG. 11
FIG. 12

FIG. 16
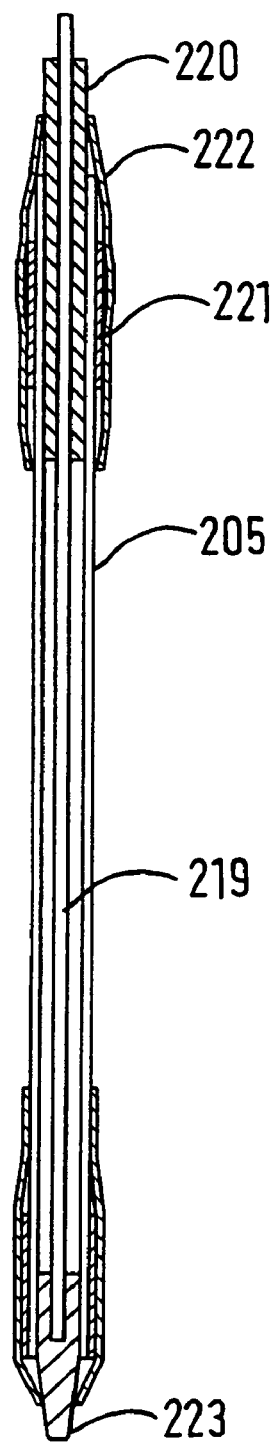

DEVICES AND METHODS FOR THE REPAIR OF ARTERIES

FIELD OF THE INVENTION

The present invention relates to devices and methods for the repair of arteries, and in particular to devices and methods for retaining grafts on arteries, methods of delivering such devices to arteries, devices for supporting catheters within arteries and devices for dilating arteries.

BACKGROUND OF THE INVENTION

For clinical applications, grafts made of woven, moulded or extruded synthetic polymeric or elastomeric materials are commonly used to replace natural tissue within a living organism which either is diseased or has suffered trauma. Commonly known in the art, grafts are sutured in place during an open surgical procedure or are held in place by stents in a combination known as a stent-graft. Some stent-grafts use barbs to fix the implant into the body conduit but successful stent-grafts can be complex and expensive to manufacture and, because of their rigidity, their use can be restricted to only straightforward surgical cases.

Stent-grafts, whose use now has a several years of history, show a tendency to migrate two to three years after implantation. Such an event currently requires major open surgery to replace the graft.

Other types of flat graft or patches are used to cover tissue damage. These grafts are also sutured or stapled in position during open surgery, but nevertheless also have a tendency to migrate.

SUMMARY OF THE INVENTION

In a first aspect of the present invention, there is provided a device for retaining a graft on an artery, comprising a first part for contacting the graft and a second part for contacting the artery when the device is pierced radially through the graft and the artery wall, the first and second parts being connected by a resilient member, wherein the resilient member biases the first and second parts towards each other into a retaining configuration such that in use the artery and the graft are retained together between the first and second parts of the device, and wherein the first and second parts are moveable into an open configuration in which they are further apart than in the retaining configuration to enable the device to be conveyed along an artery.

By graft is meant any material used to repair or support damaged or weak conduits within a living organism, including arteries and veins. The graft may be formed from woven, moulded or extruded synthetic polymeric or elastomeric materials and may be tubular or flat (i.e. a patch).

The fixator here defined is arranged so that fully invasive surgery is not required and access to a site within a living organism is achieved by minimally invasive surgery which includes endovascular, percutaneous or translumenal approaches. The fixator can be used to attach a conventional vascular graft or other endolumenal vascular implant from within the artery.

The retaining system used to fix and secure grafts consists of two components: the fixation device and an introducer.

The introducer comprises a pair of catheters which lie one within the other. The fixator catheter is flexible but has sufficient stiffness to oppose the reaction force created when the fixator pierces the graft/artery. The fixator catheter has an angled head which directs the fixator through the wall of the graft. The fixator catheter lies within the sheathing catheter which is another flexible catheter with a stiff section at its tip. When the fixator catheter is withdrawn into the sheathing catheter, the angled head of the fixator catheter is straightened by the stiff tip of the sheathing catheter.

By catheter is meant any suitable conduit or tube for inserting into a living organism to deliver or remove the devices of the present invention. The catheters are constructed of suitable flexible materials, substantially round in section and of diameters that can pass through natural body conduits or small incisions, to reach a site that may require a tubular graft or flat, patching material to effect a surgical repair to body parts.

In a second aspect of the invention, there is provided a device for supporting a catheter within an artery or arterial graft, the device having a locating member for locating the device with respect to the catheter and at least one support member for supporting the catheter on the inner wall of the artery or graft, wherein the support member and the locating member are connected by a resilient member which biases the support member towards the artery wall.

In a third aspect of the invention, there is provided a method for delivering a retaining/fixation device as defined above to a locus of a conduit (such as an artery), comprising the steps of moving said first and second part of the device into said open configuration, inserting the device into a catheter, positioning an end of the catheter at the locus, and moving the device down the catheter until the device emerges from said end of the catheter at the locus. The method may additionally comprise the step of employing a supporting device as defined above to support the catheter within the conduit.

By locus is meant the position in the conduit to which it is desired to deliver the fixation device. This may be a specific place on graft. The relevant end of the catheter may be positioned so that it touches the graft, or it may be positioned an appropriate distance from the graft (such as about 1.5 mm) to enable the fixation device to exit from the catheter and pierce the graft and then the artery without first springing into the open configuration.

The supporting device locates the catheter securely on the axis of the tubular vessel into whose wall the fixation device is to be inserted. The supporting device provides a stable platform to provide adequate lateral force for the fixation device to pierce the wall of the graft and then the natural tissue. The supporting device also fixes the angle at which the fixation device penetrates the wall of the graft.

Preferably, the supporting device preferably holds the tip of the fixator catheter firmly against the wall of the graft so that the fixation device is constrained and cannot deploy until after it has penetrated the wall of the graft.

The fixation device is constructed of a material that has sufficient elastic or shape memory recovery properties to be deformed into a substantially straight form and may be constrained in said form within a catheter. Upon ejection from the catheter, the fixation device is able to spring back to its manufactured shape to lock the graft to the natural tissue.

A preferred embodiment of the fixation device preferably consists of a plurality of wires lying parallel to each other and connected together in the centres of their long axes by welding or other mechanical fixation means such as binding with a wire or sheathing with a bush of metal or polymer. The binding or bushing means can usefully be made of a radio-opaque material such as tantalum or barium-loaded polymer.

In an alternative embodiment, the fixation device is constructed from a single piece of material which is shaped into a plurality of wires.

Two, three, four or more wires may be connected at their central portions; the free parts of the wires are arranged to curl tightly outwards to form a nearly-closed hook. The collection of hooks thus formed, when connected at the weld, resemble a double-ended marine anchor known as a 'grapnel' or grappling iron. Preferably, the weld joining the wires lies equidistant from the ends of the wires. The symmetry of the design ensures that the fixation device will not rotate or tumble in its location and those embodiments with three or more wires are stable in all dimensions.

The fixation device can be constructed of round, square or triangular section wire. All these types of construction are preferably connected in their central area, as described. A four wire version, in plan, is cruciform, the three wire is tri-form and so on.

Each wire, which is preferably constructed of an equi-atomic nickel-titanium shape memory alloy has, by elastic recovery or by thermally induced shape recovery means, a geometry which forms into a shape which when introduced through puncturable materials, retains one puncturable material in relation to other puncturable material. To puncture said materials, each wire preferably has a leading edge sharpened, the trailing edges being flat or rounded, preferably concave.

Each wire preferably has a diameter of from 0.1 mm to 0.7 mm, and most preferably about 0.4 mm. The length of each wire may be in a range from 4 mm to 25 mm, and preferably 15 mm.

In a preferred embodiment, the distance between the end of the wires at one end of the fixation device is about 1 mm in the open configuration and about 10 mm in the retaining configuration.

The wires are preferably sharpened with an oblique point of elongate ellipsoid form so that when the wires are constrained in a catheter before delivery, the bundle of wires is sharpened to a single point.

In one embodiment, a plurality of fixation devices are constrained in line in a delivery catheter and are ejected by a flexible pusher wire that pushes on the last fixator in the line, which in turn pushes on the next and so on. The number of fixators ejected is appropriate to the anatomical site and the conduit strength and size. Another embodiment involves individual fixators which may be deployed one at a time by loading the delivery catheter with a single fixator, ejecting said fixator and re-loading the catheter.

In another embodiment of the fixator, an open ring of wire is constructed from a material exhibiting either thermal effect shape recovery or elastic shape recovery and can also be used for graft fixation. The ring may be of circular or elliptical form. The dimensions of the fully deployed ring fixator are arranged so that suitable forces are generated to ensure intimate contact between graft and natural tissue. This embodiment is the simplest to construct and is potentially capable of the greatest miniaturisation for delivery in small catheters.

The ring is deformed into a straight form by urging it into the bore of a substantially straight catheter. It is then pushed through the lumen of the catheter by a pusher wire or similar means and expelled from the proximal end of the catheter. The pusher wire or similar means is capable of exerting sufficient axial force on the fixator to cause it to travel through the lumen of said catheter and penetrate at least the said graft material and the living tissue behind it. Subsequent to penetration of the graft and living tissue the ring regains its round or elliptical shape, effecting fixation of graft and living tissue.

The embodiment just described can be extended to include a plurality of rings joined end to end to form a helix. The helix has a sharpened leading tip, such that when the helix is rotated, it screws itself around the wall of the graft material. Thus in the case of a tubular graft, the helix would follow the wall of the graft to form a broken annulus while each turn of the helix would puncture the graft material and the vessel wall in turn. The said rotation can be easily achieved when the helix is fabricated from thermal effect or super-elastic shape memory alloy. Upon exiting a delivery device which constrains the wire to be nominally straight, and upon heating in the case of thermal effect material, the wire will roll itself back into the helical form. When suitably approximated to the graft material, the rolling action will thread the helix into the material.

Accordingly, in a fourth aspect of the invention, there is provided a device for retaining a graft on an artery, comprising an elongate member formed of a resilient material which biases said member into a helical configuration, at least one end of the member being sharpened to enable the member to pierce through the graft and the artery wall, wherein the member is moveable into an open configuration in which it can be conveyed along an artery.

In a fifth aspect of the invention there is provided a method for delivering a helical fixation device as defined above to a locus of a conduit, comprising the steps of moving said helical member into said open configuration, inserting the device into a catheter, positioning an end of the catheter at the locus, and moving the device down the catheter until the device emerges from said end of the catheter at the locus. The supporting device defined above is preferably employed to support the catheter within the conduit whilst the helical device is being delivered.

A specific application of the preferred fixator system is the fixation of a vascular graft in the human aorta for the repair of abdominal aortic aneurysms. The graft, typically a woven or knitted polyester, single or bifurcated tube, is attached to the fixator catheter by a simple fracturable, shearable or withdrawable connector, such as a thin suture material, the attachment being around the outside of the fixator catheter. This assembly is then placed in a sheathing catheter and introduced endovascularly to the aneurysmal site. The connector is caused to release the graft from its catheter by active mechanical means such as an integrated cutting edge or scissors. Electrical resistance heating of a small wire engaged with the catheter-to-graft attachment can be utilised to disconnect the attachment.

The leading end of the fixator catheter is then guided to the inner wall of the graft and a fixator is ejected. As the fixator is ejected it is urged through the graft and aorta, its shape changing from a nominally straight to multiple-arcuate, each arm facilitating graft fixation.

When the fixator is fully deployed the geometry is arranged so that a small compression force is developed, urging the outer surface of graft into intimate contact with the inner surface of the aorta. When intimate contact between the aorta and graft is maintained around the circumference of the graft it will ensure that blood does not leak past the graft-aorta connection. The fixators also ensure that the graft cannot migrate and any physiological forces that attempt to expand the aorta radially will be constrained by said fixator arrangement.

To achieve a leak-free graft connection, several fixators are required, introduced from inside the lumen of a body conduit. For vascular graft applications an endovascular or translumenal approach is employed, the leading edge of the catheter making a quasi-perpendicular approach to the vessel wall.

To achieve the desired angle of said catheter, a centralising mechanism (the supporting device defined above) is deployed in order to establish the spatial relationship of the catheter to the vessel.

At least one strip or one wire, which is elastically deformable, is folded length-wise in half. When the wire or strip is held at the ends but is otherwise unconstrained, it will spring into a near circular or oval shape. The folded strip can be drawn into a catheter and this action will compress it to be an almost flat bi-layer. Upon partial expulsion from the catheter, with the ends of the strip or wire still retained in the catheter, the strip or wire will spring back to its near oval shape. When it expands to its near oval shape, the strip or wire expands symmetrically about the axis of the catheter.

If the strip or wire oval is deployed within a cylindrical vessel so that it is a snug fit between the walls of the vessel, the vessel, the strip or wire oval and the catheter may be aligned coaxially. The stiffness of the strip or wire loop is such that the catheter is held firmly in the centre of the cylindrical vessel. Equally, the elasticity of the strip or wire oval is such that the oval will fit a wide range of sizes of vessel.

A single piece of wire and preferably a single wide strip is particularly useful for use in small arteries. When deployed, the strip or wire oval does not significantly reduce the flow of blood through an artery.

Preferably, a second and optionally further strip or wire loops are used, orientated so that, in plan view, the loops are coaxial but uniformly radially distributed around the axis.

The strip or wire preferably has a diameter from 0.3 mm to 5 mm, and more preferably about 1.5 mm. When in the supporting configuration, the looped embodiment of the supporting device may be from 4 mm to 50 mm when measured transversely across from one support member to another (i.e. the diameter of the loops).

The strips or wires can be pulled inside the catheter by means of a pushing or pulling wire. Equally, the retracted strips may be expelled from the constraining catheter by the pulling or pushing wire.

When retracted, the catheter enables the centralising mechanism to be transported within a narrow passage without causing interference or trauma to the passage.

Also contained within the catheter is a tube which may be made from an elastically deformable material such as PTFE or nylon. Preferably the tube is formed from super-elastic shape memory alloy such as nickel-titanium. The dimensions of this tube are such that it will allow straightened fixators to pass through its bore without interference. A typical range for the diameter of the tube is from 0.3 mm to 5 mm. Preferably, the inner diameter is about 1.5 mm and the outer diameter is about 1.7 mm. Said tube is configured such that it is extendible or retractable within the catheter. Extension and retraction is manually controlled.

The proximal end of said elastic tube is heat-treated to produce a radius that subtends an angle to the conduit wall. Preferably, the angle is between 10° and 90° and more preferably 45°, but the device will still function even if the conduit wall curves sharply away from the catheter, since glancing angles can be accommodated by the device. The present invention also relates to a medical dilation device which may be used to dilate an occluded conduit, expand a stent or facilitate circumferential conformity when fitting a tubular graft inside a vessel residing in a living organism.

Percutaneous Transluminal Coronary Angioplasty (PTCA) is a well known technique, commonly used in clinical maintenance or repair of certain fluid carrying vessels within a living organism. The technique requires the hydraulic expansion of a compliant balloon which is sited in a vessel that requires radial expansion. PTCA, although usually applied to the dilation of coronary arteries, is a technique that has been applied to other conduits requiring dilation.

A stent may be used to continually support a dilated vessel or graft, ensuring luminal patency of said vessel or graft. Stents are generally metal constructions with perforated walls that may be radially expanded when positioned in the lumen of an occluded vessel by placing a balloon inside a stent and inflating the balloon. This increases the diameter of the stent which plastically deforms due to balloon inflation.

In addition, the placement of grafts and graft-stents combinations within a natural vessel, can benefit from an internally expanding balloon to urge the outer surface of the graft or graft-stent in intimate contact with the inner wall of the said vessel.

PCTA balloons may be inflated with hydraulic media using pressures up to 20 Atmosphere. However, it is not always possible to expand the balloon with sufficient pressure to effect suitable radial expansion. For example, fibrous lesions inside a vein may be formed from a tough and tenacious fibrous material which may resist the dilatory efforts of the balloon. There is also a danger of rupture, leakage or bursting of the balloon when used at relatively high pressures.

As dilation balloons become fully dilated in arterial vessels, blood flow in the artery is prevented or severely limited. Ischemic problems may arise if blood flow is curtailed for an extended period. This is particularly relevant for vessels associated directly with the cardiovascular system such as the coronary arteries.

Accordingly, in a sixth aspect of the invention, there is provided a device for dilating an artery when delivered transluminally to a locus of an artery by means of a catheter, having a locating member for locating the device with respect to the catheter and a plurality of dilating members, each of which is connected to the locating member by a resilient member which biases the dilating member towards and into contact with the inner artery wall, wherein in use the resilient members cause the dilating members to apply outward pressure to the inner artery wall in order to dilate the artery.

The device preferably comprises at least one resilient wire disposed in a loop with the ends of the wire being locatable in an end of a catheter, wherein in use the sides of the loop contact the inner artery wall and apply outward pressure thereto in order to dilate the artery.

The inventive device employs direct mechanical connections rather than fluid pressure to expand a vessel, stent or graft or graft stent. It has the advantage of not fully occluding the blood vessel.

SUMMARY OF THE DRAWINGS

Preferred embodiments of the present invention will now be described by way of example, with reference to the accompanying drawings, in which:

FIG. 10 illustrates a stabilising device in accordance with the invention in its various configurations;

FIG. 11 illustrates apparatus for deploying a stabiliser device and for delivering fixators in accordance with the invention;

FIGS. 12 to 16 illustrate various dilators in accordance with the invention and apparatus for delivering the dilators to an artery.

DETAILED DESCRIPTION OF PREFERRED EMBODIMENT OF THE INVENTION

Figure 1:
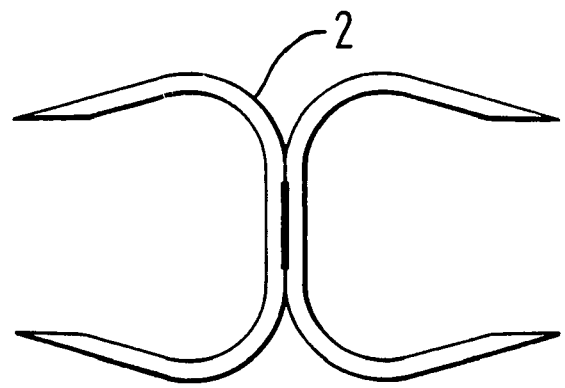
FIG. 1. shows a plan view of a wire-form fixator.

Referring to the drawings, FIG. 1. illustrates a plan view of a wire-form fixator [2], connected by welding in the central area. The end termination of the fixator are sharpened and shown in the unconstrained (retaining) configuration. The fixator [2], which is shown in its retaining configuration, includes elongated members [300] each extending between first parts [302] and second parts [304], with the first parts [302] and second parts [304] being connected by resilient members [306].

Figure 2:
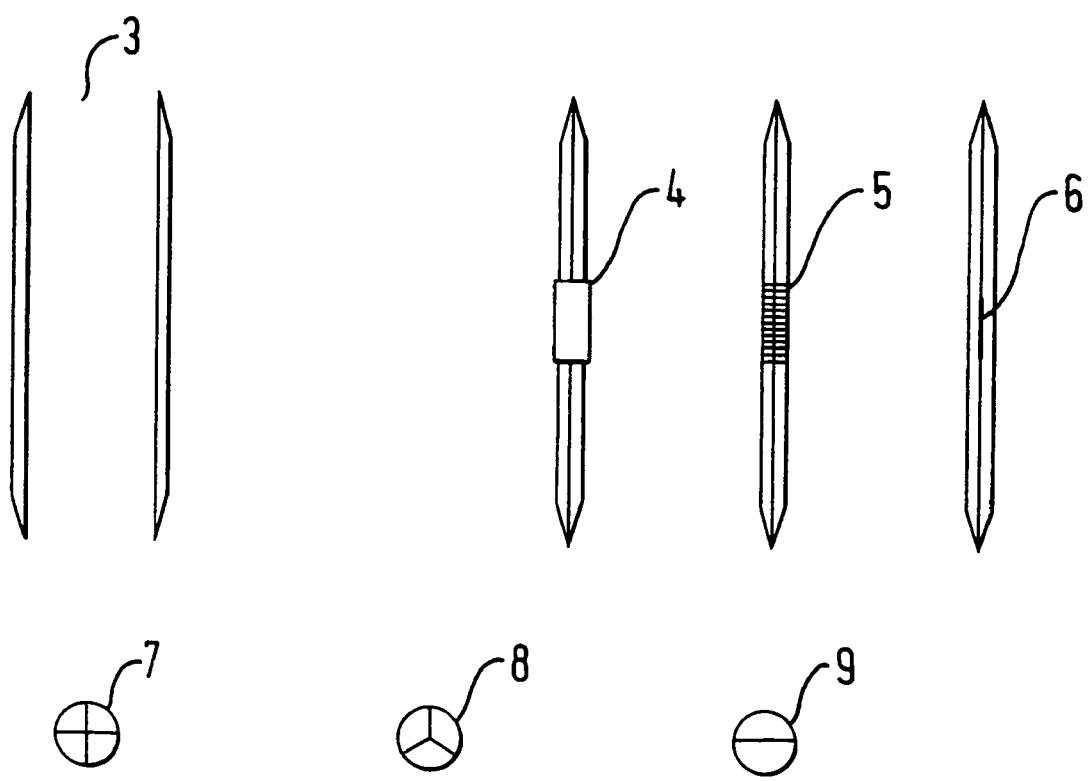
FIG. 2. shows plan views of alternative wire-form fixators.

FIG. 2. illustrates methods of connecting fixator wire-forms [3], preferably by welding [6] but alternatively binding [5], a crimping bush [4]. The cross-section is shown using four wires [7], three wires [8] and two wires [9]. All are in the constrained (open) configuration.

Figure 3:
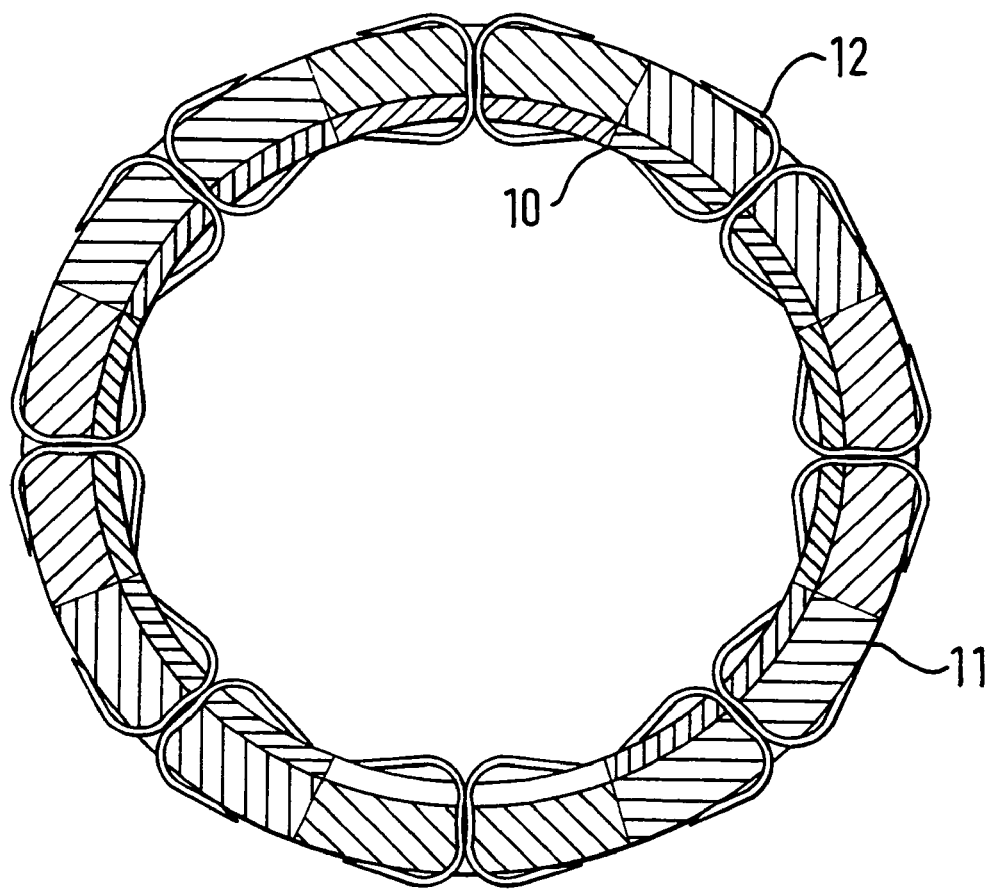
FIG. 3. shows schematically in cross-section the use of fixators in accordance with the invention.

FIG. 3. shows schematically in cross-section, fixators [12] engaging a graft [10] with aorta [11].

Figure 4:
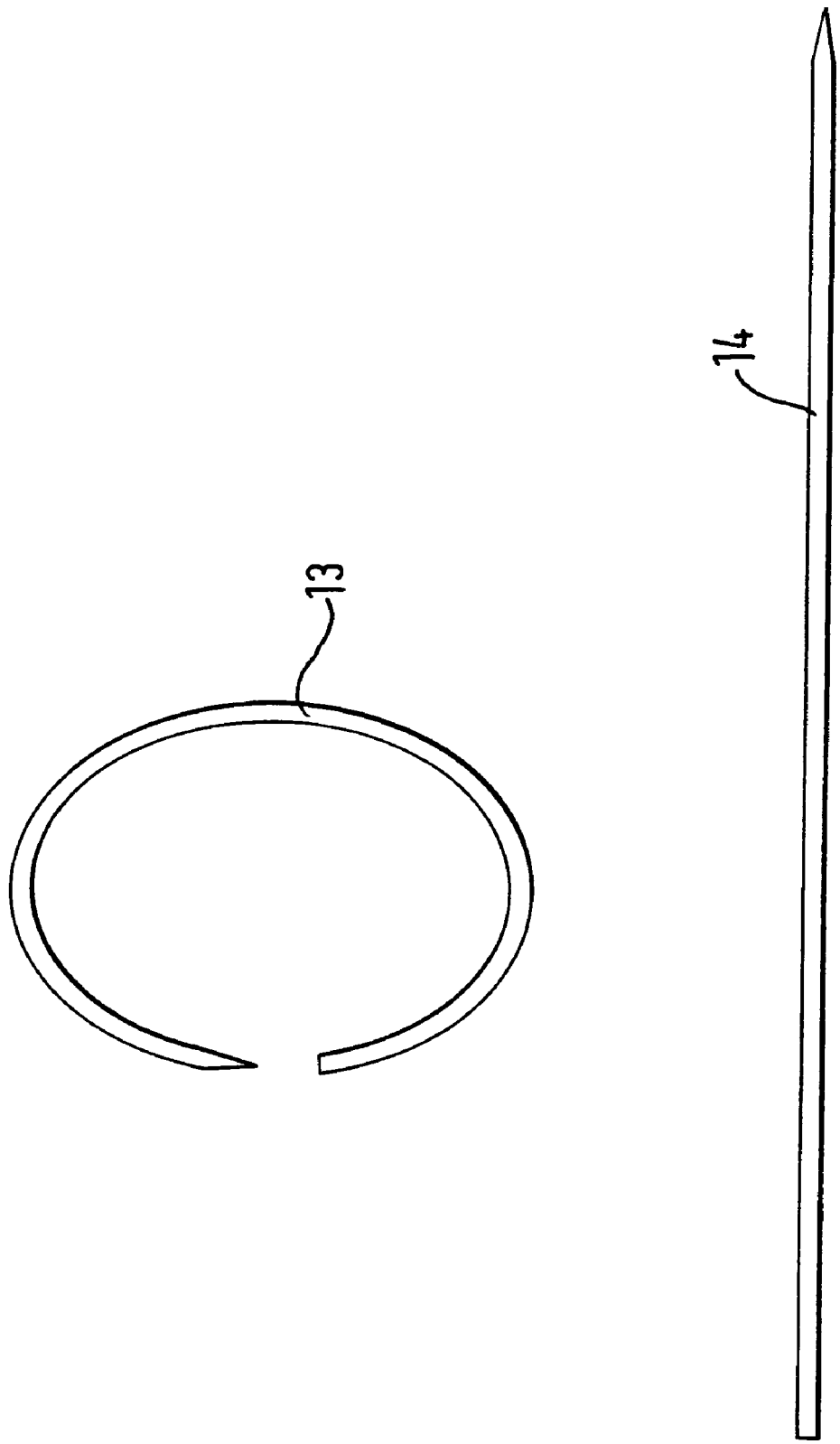
FIG. 4. shows an alternative fixator.

FIG. 4 illustrates a ring form fixator in the retaining configuration [13] and in the open configuration [14].

Figure 5:
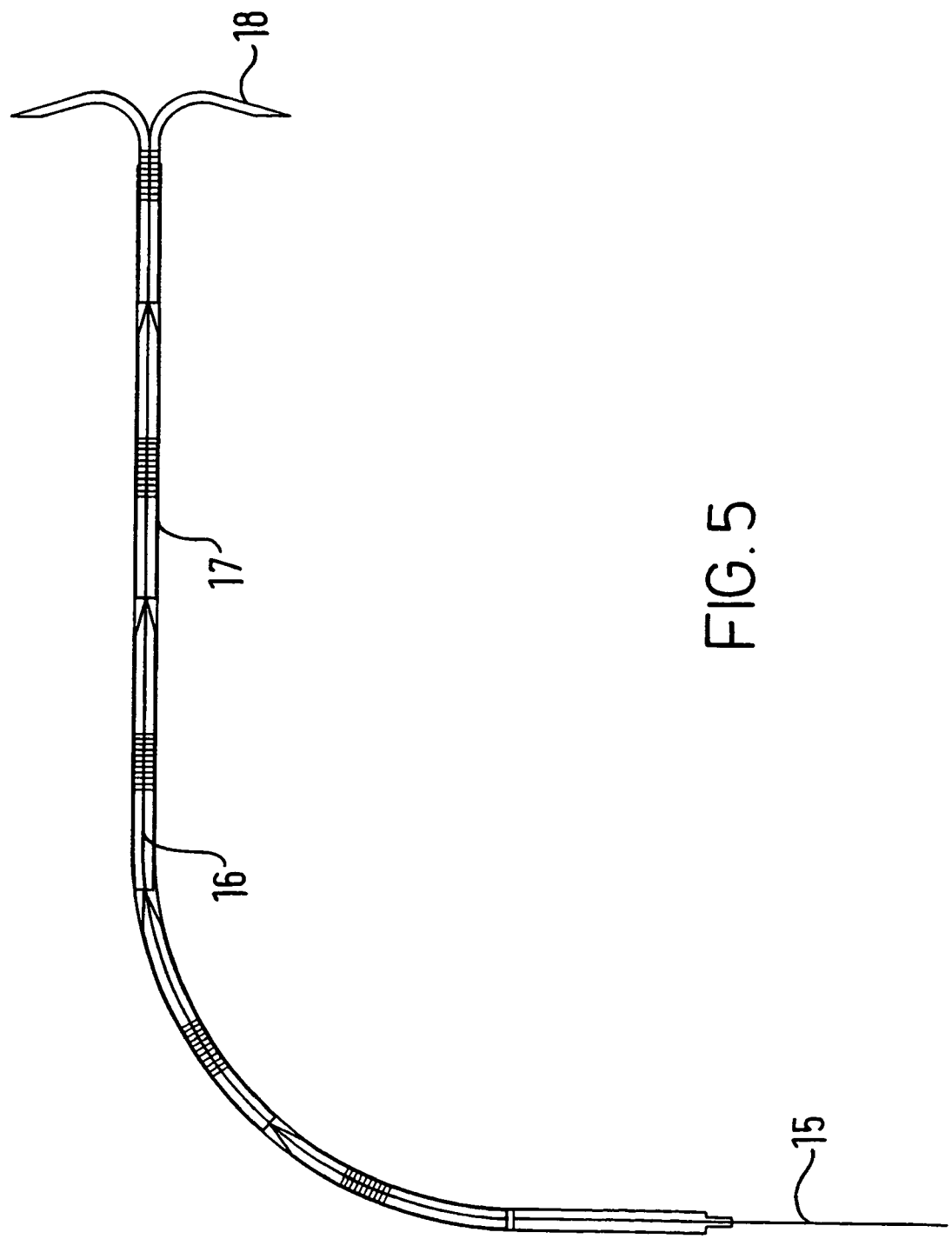
FIG. 5. shows in cross section the delivery of fixators in accordance with the invention.

FIG. 5. is a view showing ejection of fixators [18] from catheter [17] and deformed and constrained fixators [16]. The ejecting wire [15] exits from the distal end of the catheter.

Figure 6:
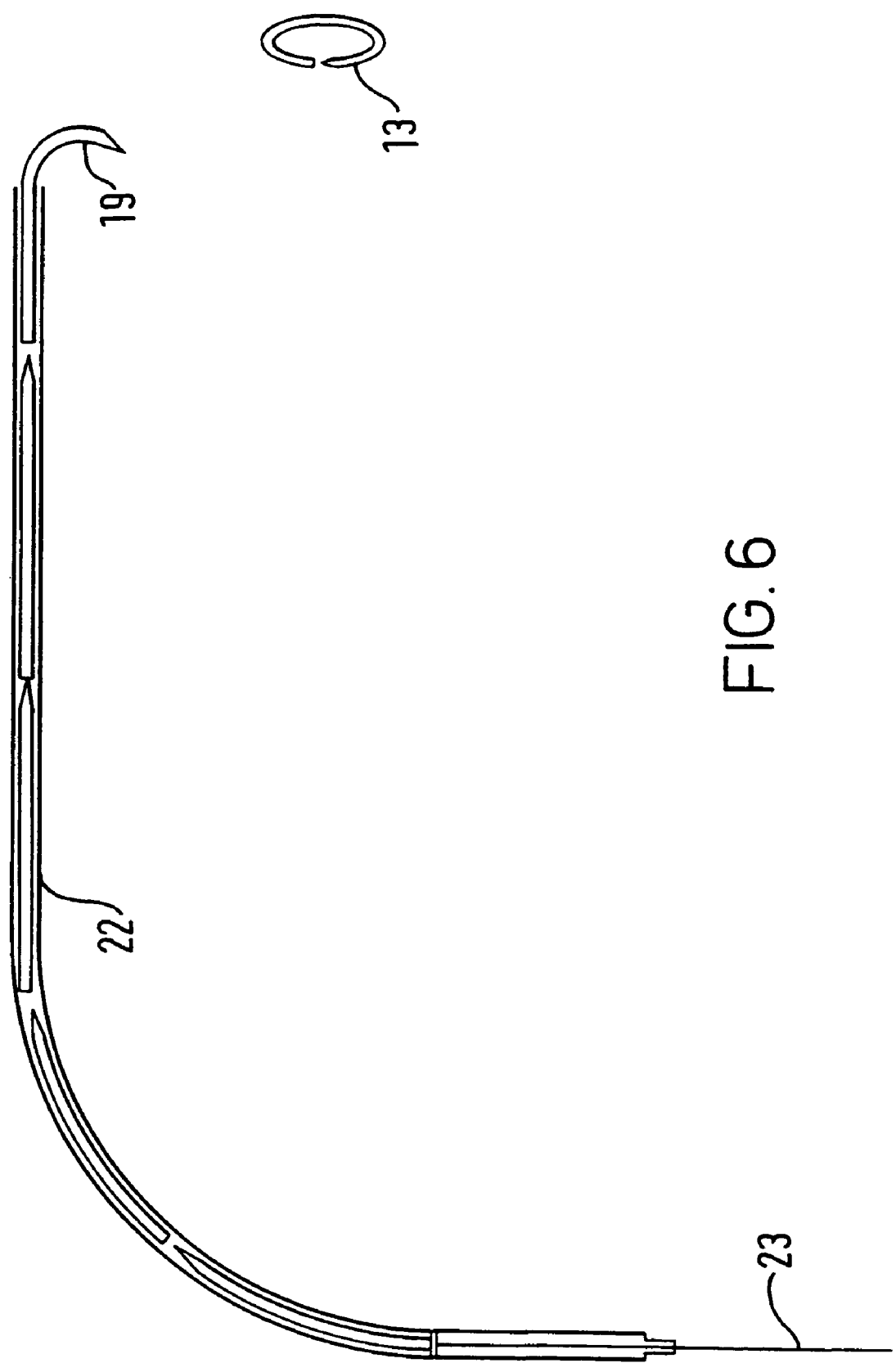
FIG. 6. shows in cross section the delivery of an alternative form of fixators in accordance with the invention.

FIG. 6. shows an alternative ring fixator [19] being ejected from the tip of the catheter [22]. Means for ejecting ring fixator is by pusher wire [23]. A fully formed ring fixator is shown [13].

Figure 7:
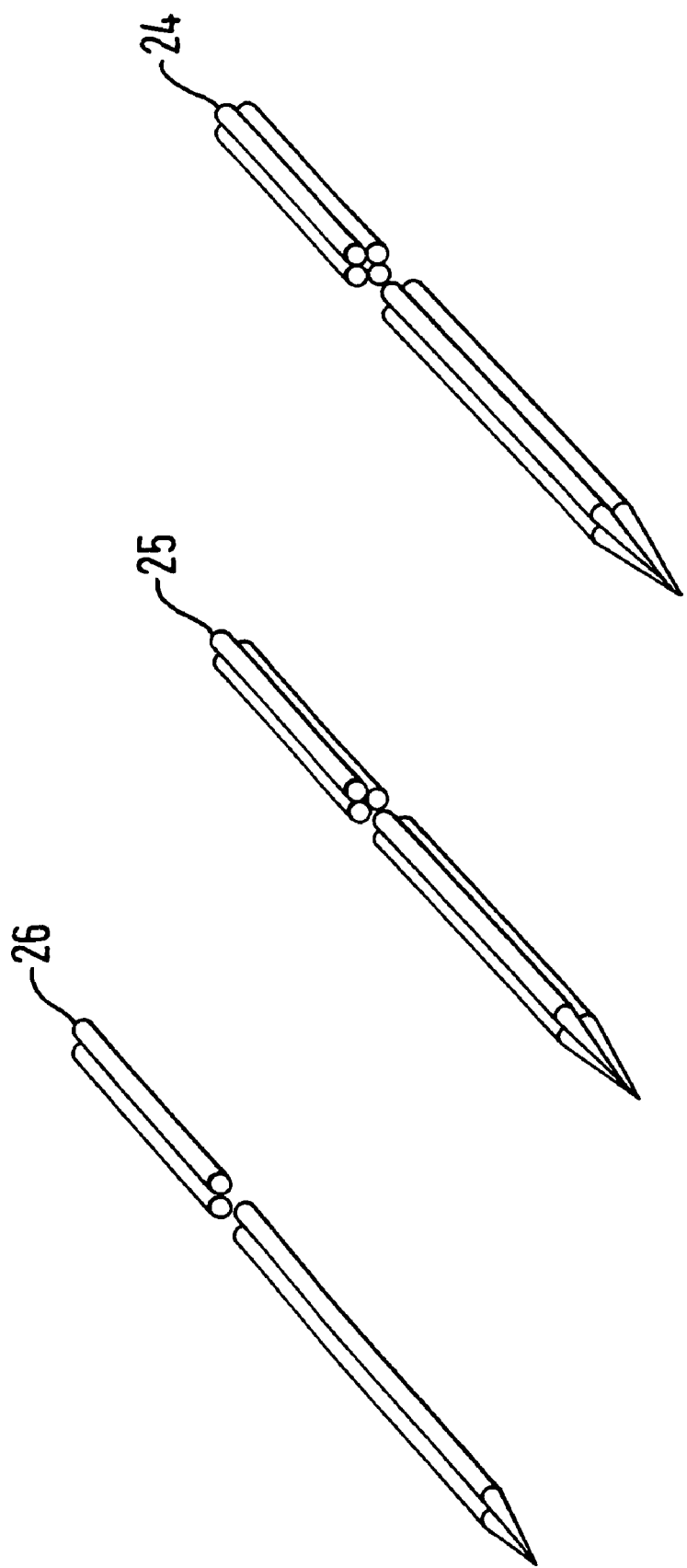
FIG. 7. is a perspective view, in partial cross-section, of various fixators in accordance with the invention.

FIG. 7. Shows embodiments of fixator arrangements in the form of two wire-form [26], three wire-forms [25] and four wire-forms [24].

Figure 8:
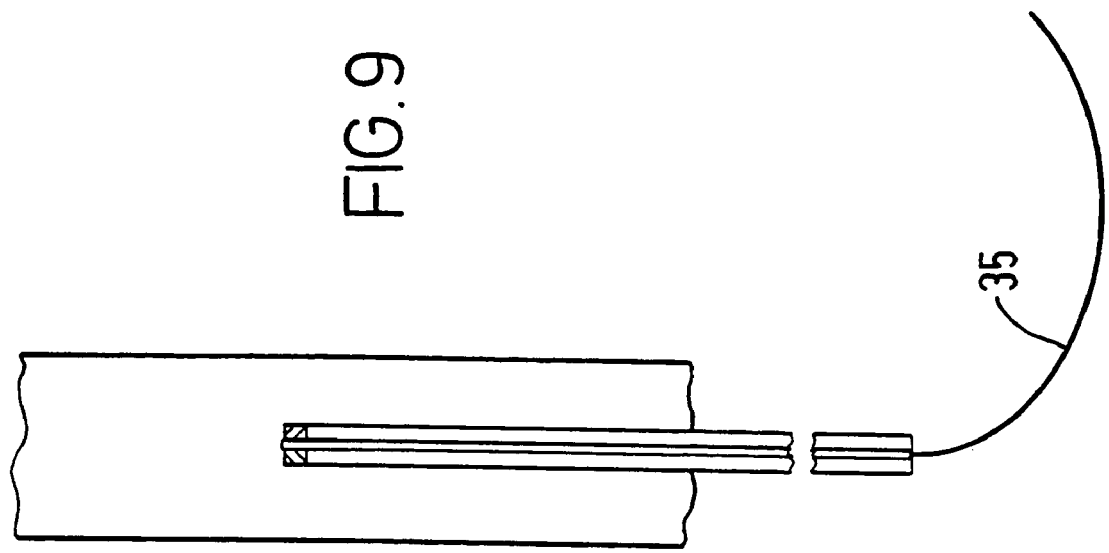
FIG. 8.

FIG. 8. Shows the embodiment whereby fixators approach an artery [33] at 90° to the long axis. An elastically deformable tube [32] forms a 90° arc when extended from its constraining catheter [34], by means of a pushing or pulling wire [35].

Figure 9:
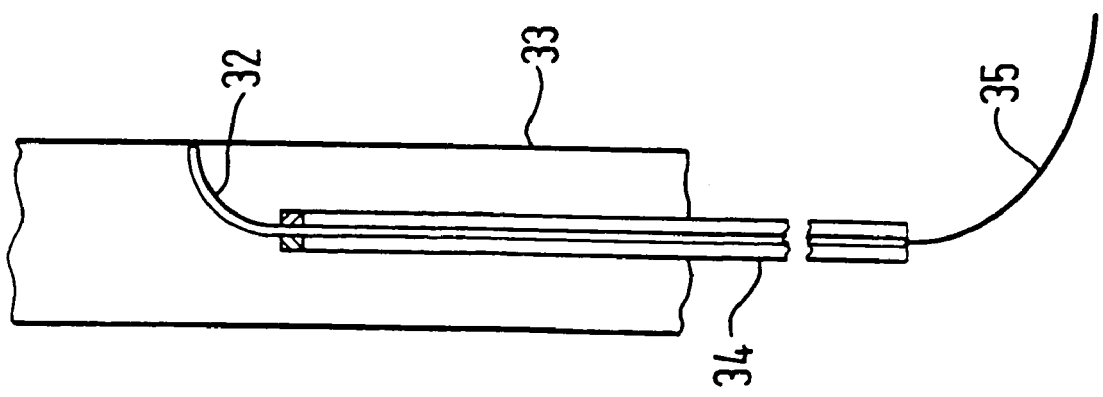
FIG. 9 illustrate a method of securing a graft to an artery in accordance with the invention.

FIG. 9. Shows a means to retract the fixator delivery tube by pulling the pushing\pulling wire [35], causing the tube to be drawn inside the catheter.

A graft fixator system will now be described in detail with particular reference to FIGS. 10 and 11.

A graft fixator system consists of a delivery system and one or a series of fixators. The delivery system is comprised of the following elements: A hand held device to control and determine fixators ejection, to deploy a stabilising device and the fixator delivery tube. The hand held controller of similar external form to a hand-held gun, consists of a trigger used to eject fixators a sliding and rotatable barrel used to deploy the fixator delivery tube\stabiliser assembly and to rotate the delivery tube assembly.

The hand-held device FIG. 11. has three functions. To eject fixators, to deploy the fixator delivery tube and to deploy the stabiliser system. When squeezed, the trigger (37) ejects fixators. The trigger mechanism is connected directly to a wire (40) which pushes against the fixators. To ensure adequate penetration of the fixators, operation of the trigger impacts the fixator by a spring-assisted release when the trigger is pulled. This mechanism is identical to the mechanical configurations found in an automatic hand pistols which also require an impacting force against a bullet cartridge. The sliding and rotatable barrel (41) deploys both stabiliser and fixators. The barrel is mechanically connected to the stabiliser deployment tube (39) and fixator eject wire (40). Linear movement of the barrel produces an equal movement of the stabiliser, deployment mechanism and fixator eject wire (39, 40).

The stabiliser (FIG. 10) consists of two elastically deformable thin strips of metal (47) which, when unconstrained form a nominally circular shape (46). The two strips are riveted together (45) at the leading edge and are riveted onto a short metal tube (49) which has been arranged to retract within a catheter sheath (48). The metal tube (49) serves as a locating member for locating the device with respect to a catheter, and the distal portions of the strips (46) define support members (320) for supporting the catheter on the inner wall of an artery or graft. The proximal portions of the strips (46) then serve as resilient members (322) which connect the locating member (49) and the support members (320), with the resilient members (322) biasing the support members (320) toward the artery wall. As the resilient members (322) bias the support members (320) toward the artery wall, they reduce the distance between the end of each support member (322) and its resilient member (322), thereby causing the support member (322) to bow radially outward with respect to the locating member (49).

The fixator delivery tube (FIGS. 8 and 9) is contained within a constraining sheath until it is push-out by a pusher-wire, operated by linear actuation of the gun-barrel. Equally, it can be drawn back into its sheath by pulling the wire. The fixator delivery tube is made from a super-elastic nickel-titanium alloy that has a pre-formed radius at its tip (32). As it is pushed out of its constraining catheter, by elastic shape recovery, the radius forms which is arranged to abut against a natural tissue wall or a graft fitted coaxially within the natural tissue wall. The stabiliser and fixator tube deployment are operated by the same push-pull wire.

To use the graft fixator, access to the living organism has to be made at a suitable site, for example, in a human being, the femoral artery, close to the groin, would be used to subtend a pathway to the arterial system. The catheter sheath containing the graft fixator delivery system, enters the vascular pathway and may be guided to an appropriate site by means of a guide-wire through the centre or on the side of the fixator delivery assembly. The delivery assembly is progressed through the organism until it reaches the required position. This may be determined by angiographic techniques or ultrasound or other suitable medical visualisation devices.

The gun-like controller barrel is then pushed forward, this deploys the cruciform stabiliser and fixator tube. The slidable barrel has two control positions. One extends the delivery tube, the other extends and deploys the stabilising cruciform device. The two positions are indicated by a graduated linear scale positioned on the static part of the barrel assembly.

Due to the radiused tip of the fixator delivery tube, as it is deployed from its constraining sheath a radius forms (due to elastic recovery) and abuts against the selected vessel wall. If the correct positioning of the fixator delivery assembly has been determined, the gun-handle trigger is depressed which ejects a fixator.

The graft fixator system is capable of ejecting one or several fixators which may be disposed around the circumference of an implanted graft to ensure that leak paths between the natural conduit and graft, are eliminated. A plurality of fixators may be used by the following means:

After one fixator is ejected, the linear\rotatable barrel is slid-back to a point indicated a graduated scale. It is then rotated and slid forward. This draws the fixator delivery tube into its sheath, constraining it as a straight-tube, rotation of the barrel also rotates the delivery tube.

Fixator deployment sequence is the same as described previously: The rotated barrel is pushed forward, the delivery tube now is extrudes from its sheath in a new position on the inner circumference of the graft. A second fixator is now deployed which is radially offset by approximately 45° relative to the first. Subsequent fixators may be positioned clockwise or anti-clockwise as long as the rotational direction remains the same for each fixator.

When sufficient fixators have been deployed, the sliding barrel is fully retracted, sheathing the delivery tube and stabilser, the entire catheter may now be withdrawn from the organism.

Preferred embodiments of dilators in accordance with the invention will be described with reference to FIGS. 12 to 16.

FIG. 12 is a schematic representation of the wire-form dilator in plan (104) and a side view (105), showing the delivery catheter (106).

Figure 13:
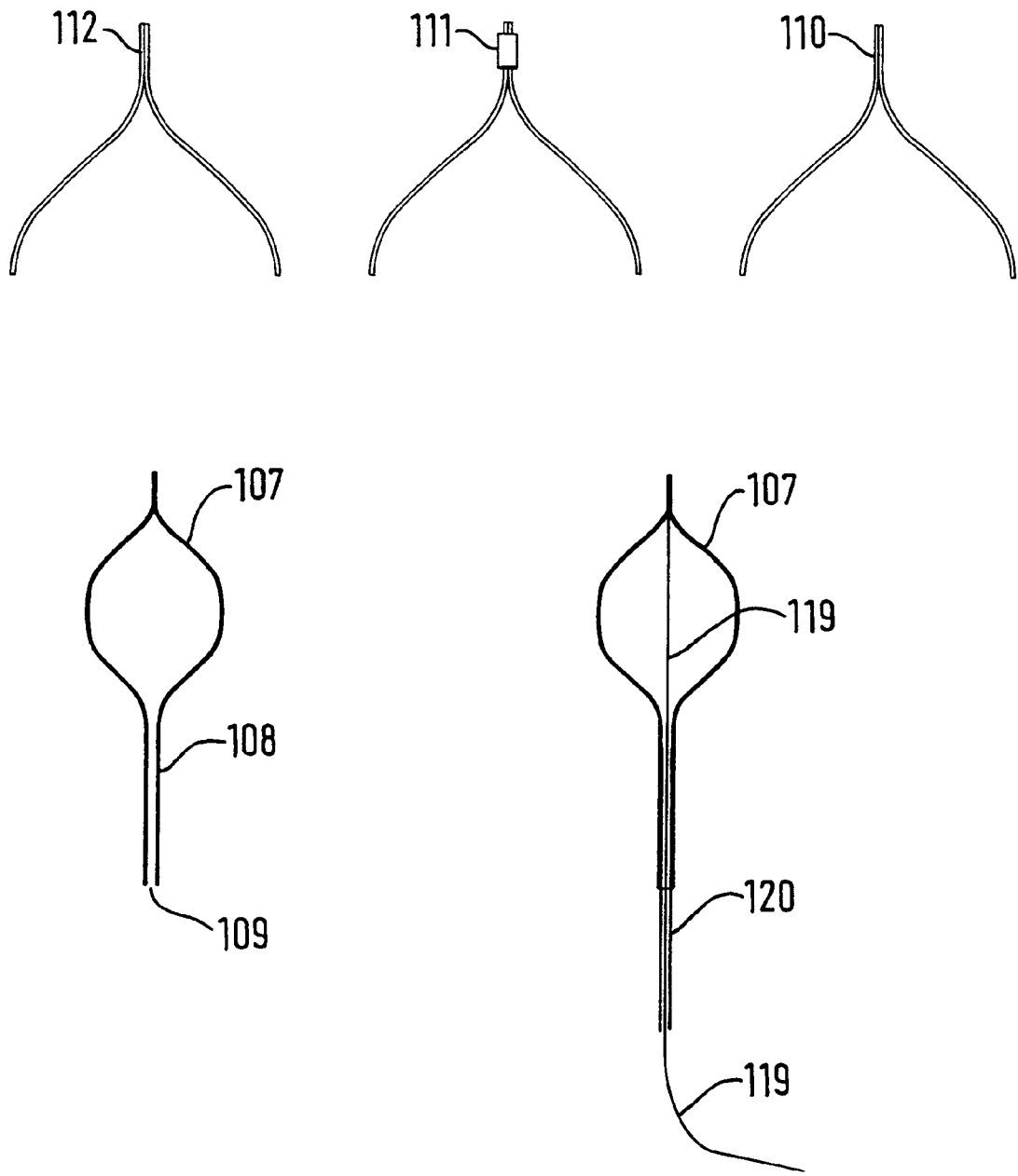

FIG. 13 illustrates methods of forming the distal end of a dilator (110-112) and shows schematically, a single wire-form dilator element (107-109) and a wire-form deployment and envelope expansion mechanism in the from of a pulling wire (119) and a pushing\pulling tube (120). Each dilator element includes a dilating member (107) having a resilient member (350) connecting the dilating member (107) to a locating member (108) and biasing the dilating member (107) towards and into contact with the inner artery wall, whereby in use the resilient members (350) cause the dilating members (107) to apply outward pressure to the inner artery wall to dilate the artery. The pulling wire (119) serves as a means for reducing the distance between each dilating member (107) and each locating member (108), thereby causing the central section of said dilating member (107) to bow radially outward with respect to the locating member (108) in order to apply increased outward pressure on the inner wall of the artery when the device is in use.

Figure 14:
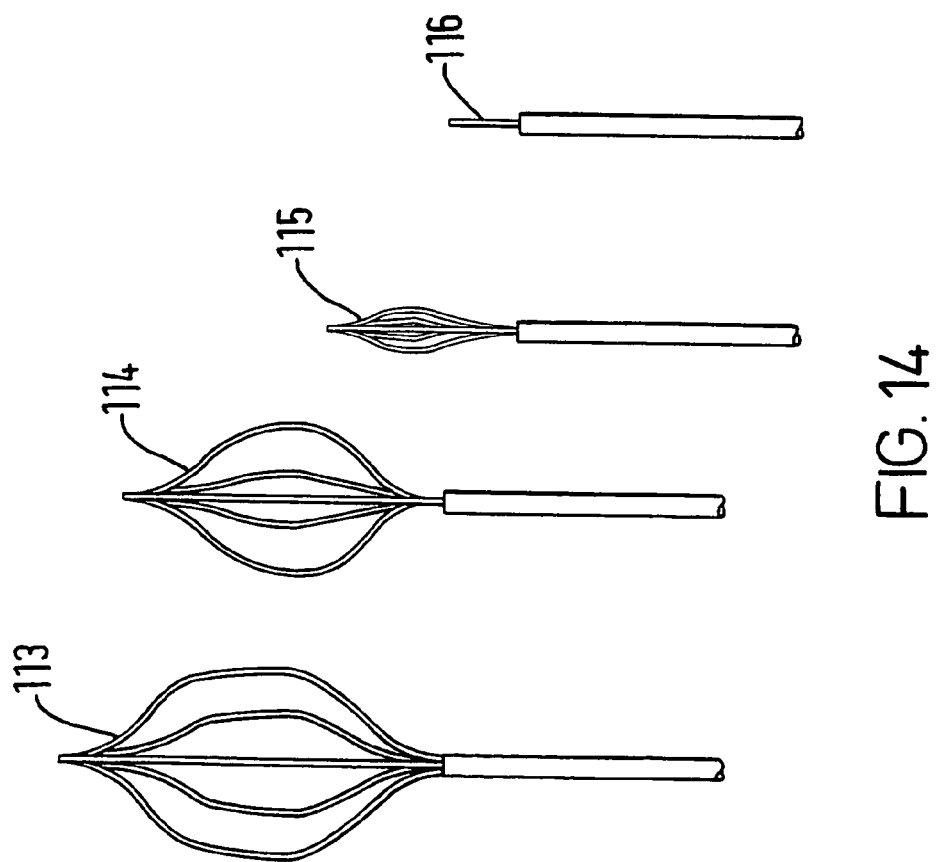

FIG. 14 illustrates schematically the wire-form dilator being drawn into its sheath or catheter (113-116).

Figure 15:
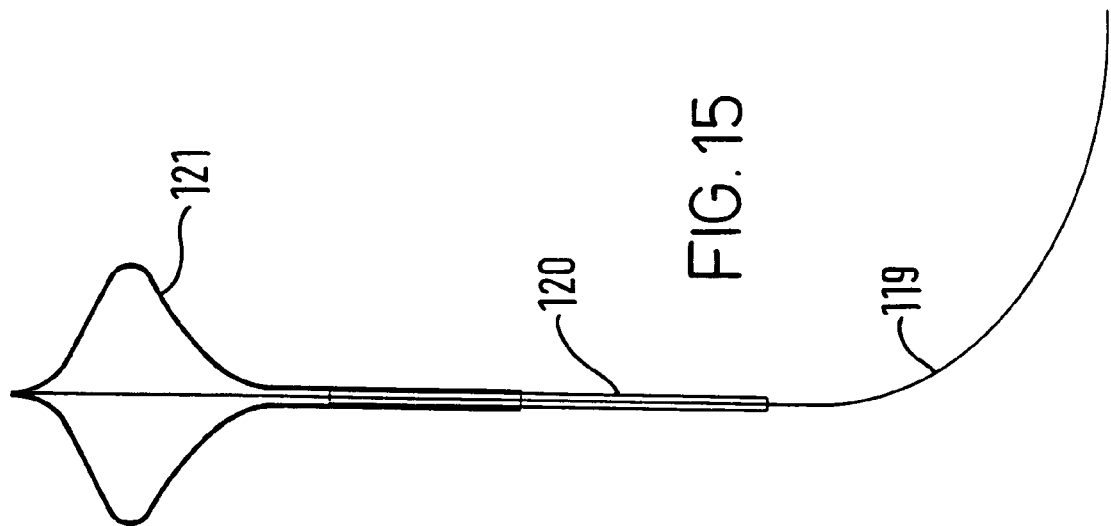

FIG. 15 illustrates schematically the use of the pulling wire (119) and pushing\pulling tube (120) to increase the wire-form envelope diameter (121).

The construction of the dilation device consists of a plurality of wires (105), or thin strips, preferably made from a super elastic alloy, pre-formed into a substantially ellipsoidal (107) shape with one end open (109) and extended (108). The other end of the dilator terminates with the plurality of wire joined together by means of welding (110), crimping with a bush (111) or binding with a suitable wire or cord (112). The wires are configured with suitable elastic recovery properties so that they may be deformed and constrained to a minimised volume for introduction and transportation within a living organism. This is achieved by pulling the wire-form inside a sheath (113-116). If the constraining influence is removed, the wires resume a shape by elastic recovery. The restraining mechanism is a sheath of suitable dimensions so that the wires may be drawn into their retaining and constraining sheath (106), by drawing them into the sheath by means of small tube (120), preferably formed from a super elastic alloy as described. The tube is connected to each of the terminal ends of the wire-form balloon by welding, riveting or hard soldering.

Another elastically deformable wire (119) is positioned inside the tube (120) and connected to the leading edge of the wire-form balloon by welding, binding or by a crimped bush. The wire (119) can slide freely through the tube (120).

A nominal outer envelope diameter of the wire-form assembly is established by virtue of the elastic shape recovery of each wire-form element.

The unconstrained, elastic recovery of the wire-form may have sufficient hoop energy to effectively expand a stent or graft or natural vessel but, by utilising a wire to pull the end tip of the wire-form balloon and at the same time preventing the trailing-end of the device from moving, the wire-form can adopt an increase in its diametrical envelope. Equally, the wire-form envelope may be reduced by preventing the pulling wire (119) from moving while pulling the tube (120), to a pre-determined position. This enables one wire-form device to be used for dilation purposes within vessels of different diameters. The range of dilation diameters required would be from 4.0 mm to 30.0 mm.

The geometry of the wire-form balloon is preferably ellipsoidal in section although the shape may be configured for particular medical situations. For example, coronary occlusive disease which requires dilation of the vessels to re-instate luminal patency, should have a nominal diameter in an adult and when in good condition of approximately 4.0 mm. However, the length of said lesions are typically up to 20 mm. A wire-form balloon for this task will be long but relatively small in diameter. Tumorous growth in the oesophagous which may need dilation and stent support as a palliative measure, requires a wire-form with a different diameter-to-length relationship, for example a diameter of from 20 to 30 mm and a length of from 50 to 60 mm.

A preferred embodiment of a wire-form balloon consists of a flexible tube or catheter (106), containing wires having a predetermined shape when unconstrained (107). Said wires may be drawn into said flexible tube and constrained within the volume of the sheath. The geometry, in plan of the wire form consists of a series of arms radiating outwards (104), from the centre of the wire-form device. The number of said arms radiating outwards can be arranged from a minimum of two to a maximum of twenty.

The wire-forms, preferably constructed from super-elastic shape memory alloy, such as nickel-titanium, or nickel-titanium-copper or nickel-titanium-copper-chromium, may be drawn within the lumen of said sheath by means of a pulling tube (120). Elastic shape recovery of the wire-forms may be sufficient to effect suitable vessel dilation; additional expansion may be facilitated by pulling the proximal end of the wire-form balloon, normal to its long axis while constraining the distal ends of the wire-forms. This expands the diameter of the wire-form (121), reducing its length.

A specific embodiment of the dilator will now be described with reference to FIG. 16. A dilator comprises a plastic tube (120) made from PTFE with an outside diameter of 1.65 mm and an internal diameter of 1 mm. The catheter is between 1 m and 1.5 m long. Through the catheter runs a 316 stainless steel or Nitinol actuator wire (219) of 0.5 mm in diameter. At one end of the wire is attached a proprietary handle, commonly known as a 'torquer'. This end is intended to remain in the hands of the medical practitioner.

At the other end of the catheter a set of thirteen wires (205) made of superelastic Nitinol, 0.3 mm in diameter by 70 mm long are arranged circumferentially around the catheter and parallel to the axis of the catheter. The wires are retained on the end of the catheter by means of a stainless steel sleeve (221) which is 5 mm in length and has a wall thickness of 0.2 mm. The sleeve is crimped around the 13 Nitinol wires such that the wires project 60 mm beyond the end of the catheter. In order to provide a smooth outer surface to the region of the crimp, an elastic or heat-shrinking sleeve (222) of 15 mm length is applied over the sleeve.

The actuator wire emerges the end of the catheter and lies at the centre of the 13 Nitinol wires so that they are uniformly radially distributed about it. The tip of the actuator wire is crimped or glued into a stainless steel bush (223) of 1.65 mm diameter and 8.5 mm in length. The actuator wire does not pass through the bush. The tip of the bush is rounded to provide a smooth, atraumatic tip for the device.

The 13 Nitinol wires are radially distributed around the bush and are attached to it by means of a second sleeve which is identical to that retaining the wires to the end of the catheter. Similarly, a heat shrink sleeve of 15 mm length is applied over the sleeve and bush to render the surface of the region smooth.

The Nitinol wires may be pre-formed to have a slight bend in the centre of their bodies which, during assembly, is arranged to be directed away from the main axis of the whole device. In this embodiment, the wires are mounted firmly in a bushes at either end of their extent. The bushes are drilled or have otherwise formed in them holes which are uniformly radially arranged to retain the Nitinol wires in their preferred orientation. The wires are securely fastened in the radially arranged holes by means of gluing crimping welding or other permanent attachment means. Moreover, a bush at one end of the wires (the first bush) is firmly attached to the tip of the catheter by gluing, crimping, force-fitting or sleeving so that it cannot rotate. The second bush is firmly attached to the actuator so that similarly, it cannot rotate. The actuator wire is preferably not circular so that an aperture with a mating internal form can be used in the catheter or, conveniently, the centre of the first bush, so as to prevent rotation of the actuator wire about the axis. The actuator wire can conveniently have a cross section which is oval or rectangular, although other shapes are possible.

The advantage of this embodiment is that the 13 Nitinol wires are more likely to remain uniformly distributed around their central core. This is of particular significance when the actuator wire has been pulled and the 13 Nitinol wires are caused to bulge out laterally from the central axis of the device.

It is desirable that all embodiments of the dilator have sufficient space through the lumen of the catheter, between the Nitinol wires and through the bush at the tip of the device to permit the device to be threaded over a guide wire typically of 0.035" diameter (0.88 mm). This can be effected by introducing an additional lumen to the catheter, by employing a hollow actuator wire or by selecting actuator and guide wire size that will fit appropriately within the catheter.

For the avoidance of doubt, "artery" as used herein means any vessel or conduit in a living organism, including but not limited to arteries, veins and capillaries.

The invention claimed is:

1. A fixator for retaining a graft on an artery comprising:
   a. a plurality of first parts for contacting the graft when the device is pierced radially through the graft and the artery wall,
   b. at least one second part for contacting the artery when the device is pierced radially through the graft and the artery wall, and
   c. a resilient member connecting the first and second parts, wherein the first and second parts each terminate in tips opposite the resilient member, with at least one of the tips being sharpened to enable the tip to pierce a graft and an artery, and wherein:
      (1) the resilient member biases the first and second parts towards each other into a retaining configuration such that in use the artery and the graft are retained together between the first and second parts of the device, and
      (2) the first and second parts are moveable into an open configuration in which they are:
         (a) at least substantially disposed along a common axis with the resilient member, and
         (b) further apart than in the retaining configuration to enable the device to be conveyed along an artery, and
      (3) only the first and second parts extend from the resilient member, such that all structures extending from the resilient member move between the retaining and open configurations,
   and wherein the resilient member has a cross-sectional area at least substantially equal to the greater of:
   the sums of the cross-sectional areas non-sharpened portions of the first parts when the first parts are in their open configuration, and
   ii. the sums of the cross-sectional areas non-sharpened portions of the second parts when the second parts are in their open configuration.

2. The fixator of claim 1 wherein in the retaining configuration at least one of the first and second parts forms an arcuate shape.

3. The fixator of claim 1 wherein at least a portion of both the first and second parts is sharpened to enable said parts to pierce a graft and an artery.

4. The fixator of claim 1 wherein the device is formed from one or more wires, the wires having lengths extending from the first parts to the second parts.

5. The fixator of claim 1 wherein the device is formed from a shape memory alloy.

6. The fixator of claim 1 wherein the device has a plurality of second parts.

7. The fixator of claim 6 wherein said plurality of parts are integral or welded together.

8. The fixator of claim 6 wherein the device has equal numbers of first and second parts.

9. The fixator of claim 8 which is formed of a plurality of wires, each wire comprising a first part, a resilient member and a second part, wherein the plurality of wires are linked together by a weld, a sheath, a bush, a crimp or by wire.

10. The fixator of claim 1 in combination with a graft, wherein the fixator extends through the graft with its first parts contacting the surface of the graft, and with the resilient member extending through the graft.

11. The fixator of claim 1 wherein the first parts, second parts, and resilient member are all at least substantially coaxial when the first and second parts are in their open configuration.

12. The fixator of claim 1 wherein the first parts are adjacently aligned in abutment with each other when the first and second parts are in their open configuration.

13. The fixator of claim 1 wherein:
   a. the first parts are adjacently aligned in abutment with each other, and
   a. the second parts are adjacently aligned in abutment with each other,
   when the first and second parts are in their open configuration.

14. The fixator of claim 1 wherein the fixator, when in the retaining configuration, is shorter along a direction aligned along the common axis than when in the open configuration.

15. The fixator of claim 1 wherein at least one of the first and second parts is sharpened at a location most distant from the resilient member, as measured along a length extending from the resilient member along the first and second parts.

16. A kit comprising:
A. A fixator for retaining a graft on an artery, the fixator including:
   a. a plurality of first parts for contacting the graft when the device is pierced radially through the graft and the artery wall,
   b. at least one second part for contacting the artery when the device is pierced radially through the graft and the artery wall, and
   c. a resilient member connecting the first and second parts,
   wherein at least a portion of at least one of the first and second parts is sharpened to enable said part to pierce a graft and an artery, and wherein:
   (1) the resilient member biases the first and second parts towards each other into a retaining configuration such that in use the artery and the graft are retained together between the first and second parts of the device, and
   (2) the first and second parts are moveable into an open configuration in which they are:
      (a) at least substantially disposed along a common axis with the resilient member, and
      (b) further apart than in the retaining configuration to enable the device to be conveyed along an artery,
B. at least one of:
   a. a device for supporting a catheter within an artery or arterial graft, the device including:
      (1) a locating member for locating the device with respect to a catheter,
      (2) a plurality of support members for supporting a catheter on the inner wall of the artery or graft,
      (3) a resilient member connecting the locating member and the support members, wherein the resilient member is configured to bias the support members towards the artery wall,
      (4) means for reducing the distance between the end of each support member distal to the locating member and the end of said support member proximate the locating member, thereby causing a central section of said support member to bow radially outward with respect to the locating member;
   b. a device for dilating an artery when delivered translumenally to a locus of an artery by means of a catheter, the device including:
      (1) a locating member for locating the device with respect to a catheter;
      (2) a plurality of dilating members,
      (3) a resilient member connecting the dilating members to the locating member and configured to bias the dilating member towards and into contact with the inner artery wall, whereby in use the resilient members cause the dilating members to apply outward pressure to the inner artery wall and dilate the artery,
      (4) means for reducing the distance between the end of each dilating member distal to the locating member and the end of said dilating member proximate the locating member, thereby causing the central section of said dilating member to bow radially outward with respect to the locating member in order to apply increased outward pressure on the inner wall of the artery when the device is in use.

17. A fixator for retaining a graft on an artery consisting of elongated members, each elongated member extending between at least one first part and at least one second part terminating in tips, wherein the tip of at least one of the first and second parts is sharpened, wherein each elongated member is capable of:
   a. an open configuration wherein:
      (1) the first and second parts are distant and are at least substantially aligned along a common axis,
      (2) the first parts are adjacently situated with their lengths in abutment,
      (3) the second parts are adjacently situated with their lengths in abutment,
      (4) the first parts and second parts of the elongated members are all at least substantially coaxial when the elongated members are in their open configuration,
      (5) the fixator has an at least substantially uniform cross-sectional area as it extends from its first parts to its second parts; and
   b. a retaining configuration wherein the first and second parts are closely spaced, and wherein each elongated member is biased towards the retaining configuration,
      whereby the elongated members of the fixator may in the open configuration be inserted into the circumference of a graft-bearing artery to pierce the graft and artery, and may then be released to move to the retaining configuration, wherein the graft and artery are maintained between the first and second parts.

18. The fixator of claim 17 wherein each elongated member extends entirely between its first and second parts, whereby its first and second parts define its terminal ends.

19. The fixator of claim 17 wherein the fixator, when in the retaining configuration, is shorter along a direction aligned along the common axis than when in the open configuration.

20. A fixator for retaining a graft on an artery, the fixator comprising elongated members:
   a. extending between first and second parts, at least one of the first and second parts being sharpened, and
   b. being connected between their first and second parts, wherein each elongated member moves between:
   (1) an open configuration wherein:
      (a) the elongated member and its first and second parts are at least substantially oriented along a linear axis with its first and second parts distantly spaced, and
      (b) the fixator has an at least substantially uniform cross-sectional area between the first and second parts and along the connection therebetween,
   (2) a retaining configuration wherein the elongated member is bent so that its first and second parts are closely spaced,
   and wherein:
   i. only the first and second parts extend from the connection between the elongated members, and
   ii. the elongated members, when in their open configurations, have their first parts adjacently situated in abutment and their second parts adjacently situated in abutment;
   whereby the elongated members of the fixator may in the open configuration be inserted into the circumference of a graft-bearing artery to pierce the graft and artery, and may then be moved to the retaining configuration to situate the graft and artery between the first and second parts.

21. The fixator of claim 20 wherein each elongated member is normally biased into the retaining configuration.

22. The fixator of claim 20 wherein the first parts and second parts of the elongated members are all at least substantially coaxial when the elongated members are in their open configuration.

23. The fixator of claim 20 wherein the fixator, when in the retaining configuration, is shorter along a direction aligned along the linear axis than when in the open configuration.

24. The fixator of claim 20 which is formed of wires, each wire including:
   a. one of the first parts, and
   b. one of the second parts, wherein the wires are connected between their first and second parts by a weld, a sheath, a bush, a crimp or by wire.

25. The fixator of claim 20 wherein at least one of the first and second parts is sharpened at a location most distant from the connection between the first and second parts, as measured along a length extending from the connection along the first and second parts.

* * * * *